(12) United States Patent
Cote, Sr. et al.

(10) Patent No.: US 7,887,519 B2
(45) Date of Patent: Feb. 15, 2011

(54) VALVE WITH INTERNAL LIFTER

(75) Inventors: Andrew L. Cote, Sr., Merrimack, NH (US); Brian L. Newton, Woonsocket, RI (US)

(73) Assignee: Nypro Inc., Clinton, MA (US)

( * ) Notice: Subject to any disclaimer, the term of this patent is extended or adjusted under 35 U.S.C. 154(b) by 538 days.

(21) Appl. No.: 11/329,364

(22) Filed: Jan. 10, 2006

(65) Prior Publication Data

US 2006/0264841 A1 Nov. 23, 2006

Related U.S. Application Data

(60) Provisional application No. 60/644,068, filed on Jan. 14, 2005.

(51) Int. Cl.
 *A61M 5/00* (2006.01)
(52) U.S. Cl. ............................ 604/247; 604/246
(58) Field of Classification Search .................. 604/246, 604/247
 See application file for complete search history.

(56) References Cited

U.S. PATENT DOCUMENTS

| | | | |
|---|---|---|---|
| 2,594,405 A | 4/1952 | Deters | 137/53 |
| 2,693,801 A | 11/1954 | Foreman | 128/214 |
| 2,705,501 A | 4/1955 | Frizsch et al. | 137/113 |
| 2,756,740 A | 7/1956 | Deane | 128/1 |
| 2,899,975 A | 8/1959 | Fernandez | 137/543.17 |
| 2,999,499 A | 9/1961 | Willett | 128/214 |
| 3,087,492 A | 4/1963 | Garth | 128/350 |
| 3,105,511 A | 10/1963 | Murphy, Jr. | 137/399 |
| 3,192,949 A | 7/1965 | De See | 137/540 |
| 3,385,301 A | 5/1968 | Harautuneian | 128/349 |
| 3,399,677 A | 9/1968 | Gould et al. | 128/349 |
| 3,416,567 A | 12/1968 | Von Dardel et al. | 137/604 |
| 3,506,005 A | 4/1970 | Gilio et al. | 128/214 |
| 3,538,950 A | 11/1970 | Porteners | 137/608 |
| 3,570,484 A | 3/1971 | Steer | 128/214 |
| 3,572,375 A | 3/1971 | Rosenberg | 137/512 |
| 3,726,282 A | 4/1973 | Patel | 128/349 BV |
| 3,806,086 A | 4/1974 | Cloyd | 251/149.7 |
| 3,831,629 A | 8/1974 | Mackal et al. | 137/525 |
| 3,838,843 A | 10/1974 | Bernhard | 251/149.1 |
| 3,923,065 A | 12/1975 | Nozick et al. | 128/348 |
| 3,965,910 A | 6/1976 | Fischer | 128/349 R |
| 3,994,293 A | 11/1976 | Ferro | 128/214 R |
| 4,063,555 A | 12/1977 | Ulinder | 128/214 R |
| 4,080,965 A | 3/1978 | Phillips | 128/214 D |
| 4,094,195 A | 6/1978 | Friswell et al. | 73/422 GC |

(Continued)

FOREIGN PATENT DOCUMENTS

EP 0268480 A1 5/1998

(Continued)

*Primary Examiner*—Nicholas D Lucchesi
*Assistant Examiner*—Victoria P Campbell
(74) *Attorney, Agent, or Firm*—Sunstein Kann Murphy & Timbers LLP

(57) ABSTRACT

A medical valve having a close mode and an open mode includes a housing having a proximal end, a distal end, and an interior. The valve also has a valve mechanism within the interior. In illustrative embodiments, the valve mechanism has a gland member and a lifter member. The lifter member moves the gland member toward the proximal end of the housing as the valve transitions from the closed mode to the open mode.

15 Claims, 10 Drawing Sheets

U.S. PATENT DOCUMENTS

| | | | |
|---|---|---|---|
| 4,094,196 A | 6/1978 | Friswell | 73/422 GC |
| 4,116,201 A | 9/1978 | Shah | 128/351 |
| 4,121,585 A | 10/1978 | Becker, Jr. | 128/214 R |
| 4,143,853 A | 3/1979 | Abramson | 251/149.1 |
| 4,223,808 A | 9/1980 | Williams et al. | 222/88 |
| 4,300,571 A | 11/1981 | Waldbillig | 128/673 |
| 4,324,239 A | 4/1982 | Gordon et al. | 128/214 R |
| 4,333,455 A | 6/1982 | Bodicky | 128/214.4 |
| 4,334,551 A | 6/1982 | Pfister | 137/614.03 |
| 4,344,435 A | 8/1982 | Aubin | 128/350 R |
| 4,387,879 A | 6/1983 | Tauschinski | 251/149.1 |
| 4,401,432 A | 8/1983 | Schwartz | 604/89 |
| 4,421,296 A | 12/1983 | Stephens | 251/149.7 |
| 4,496,348 A | 1/1985 | Genese et al. | 604/167 |
| 4,498,658 A | 2/1985 | Mikiya | 251/149.6 |
| 4,534,758 A | 8/1985 | Akers et al. | 604/85 |
| 4,535,820 A | 8/1985 | Raines | 137/854 |
| 4,550,785 A | 11/1985 | Hibbard et al. | 173/134 |
| 4,551,136 A | 11/1985 | Mandl | 604/141 |
| 4,585,435 A | 4/1986 | Vaillancourt | 604/27 |
| 4,596,557 A | 6/1986 | Pexa | 604/86 |
| 4,611,973 A | 9/1986 | Birdwell | 417/342 |
| 4,617,015 A | 10/1986 | Foltz | 604/100 |
| 4,661,110 A | 4/1987 | Fortier et al. | 604/9 |
| 4,675,003 A | 6/1987 | Hooven | 604/9 |
| 4,681,132 A | 7/1987 | Lardner | 137/271 |
| 4,683,905 A | 8/1987 | Vigneau et al. | 137/329 |
| 4,683,916 A | 8/1987 | Raines | 137/854 |
| 4,698,061 A | 10/1987 | Makaryk et al. | 604/408 |
| 4,710,168 A | 12/1987 | Schwab et al. | 604/99 |
| 4,712,583 A | 12/1987 | Pelmulder et al. | 137/852 |
| 4,743,235 A | 5/1988 | Waldbillig et al. | 604/250 |
| 4,745,950 A | 5/1988 | Mathieu | 137/798 |
| 4,749,003 A | 6/1988 | Leason | 137/854 |
| 4,752,287 A | 6/1988 | Kurtz et al. | 604/99 |
| 4,752,292 A | 6/1988 | Lopez et al. | 604/244 |
| 4,758,224 A | 7/1988 | Siposs | 604/119 |
| 4,776,369 A | 10/1988 | Lardner et al. | 137/515.5 |
| 4,809,679 A | 3/1989 | Shimonaka et al. | 128/4 |
| 4,816,020 A | 3/1989 | Brownell | 137/112 |
| 4,819,684 A | 4/1989 | Zaugg et al. | 137/112 |
| 4,850,978 A | 7/1989 | Dudar et al. | 604/201 |
| 4,874,377 A | 10/1989 | Newgard et al. | 604/167 |
| 4,915,687 A | 4/1990 | Sivert | 604/83 |
| 4,917,668 A | 4/1990 | Haindl | 604/167 |
| 4,935,010 A | 6/1990 | Cox et al. | 604/122 |
| 4,966,199 A | 10/1990 | Ruschke | 137/843 |
| 5,006,114 A | 4/1991 | Rogers et al. | 604/167 |
| 5,041,087 A | 8/1991 | Loo et al. | 604/83 |
| 5,048,537 A | 9/1991 | Messinger | 128/673 |
| 5,049,128 A | 9/1991 | Duquette | 604/83 |
| 5,059,175 A | 10/1991 | Hanover et al. | 604/891.1 |
| 5,065,783 A | 11/1991 | Ogle, II | 137/68.1 |
| 5,080,654 A | 1/1992 | Picha et al. | 604/167 |
| 5,085,645 A | 2/1992 | Purdy et al. | 604/167 |
| 5,100,394 A | 3/1992 | Dudar et al. | 604/283 |
| 5,108,380 A | 4/1992 | Herlitze et al. | 604/283 |
| 5,122,123 A | 6/1992 | Vaillancourt | 604/192 |
| 5,127,904 A | 7/1992 | Loo et al. | 604/83 |
| 5,147,333 A | 9/1992 | Raines | 604/249 |
| 5,171,230 A | 12/1992 | Eland et al. | 604/250 |
| 5,184,652 A | 2/1993 | Fan | 141/21 |
| 5,199,947 A | 4/1993 | Lopez et al. | 604/56 |
| 5,201,715 A | 4/1993 | Masters | 604/175 |
| 5,203,775 A | 4/1993 | Frank et al. | 604/256 |
| 5,215,538 A | 6/1993 | Larkin | 604/249 |
| 5,221,271 A | 6/1993 | Nicholson et al. | 604/283 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A | 12/1993 | Thomas et al. | 604/213 |
| 5,280,876 A | 1/1994 | Atkins | 251/149.1 |
| 5,300,034 A | 4/1994 | Behnke et al. | 604/167 |
| 5,320,328 A | 6/1994 | Decloux et al. | 251/326 |
| 5,330,435 A | 7/1994 | Vaillancourt | 604/167 |
| 5,349,984 A | 9/1994 | Weinheimer et al. | 137/543.21 |
| 5,360,413 A | 11/1994 | Leason et al. | 604/249 |
| 5,380,306 A | 1/1995 | Brinon | 604/244 |
| 5,390,898 A | 2/1995 | Smedley et al. | 251/149.6 |
| 5,401,255 A | 3/1995 | Sutherland et al. | 604/247 |
| 5,439,451 A | 8/1995 | Collinson et al. | 604/247 |
| 5,441,487 A | 8/1995 | Vedder | 604/167 |
| 5,465,938 A | 11/1995 | Werge et al. | 251/149.1 |
| 5,474,536 A | 12/1995 | Bonaldo | 604/86 |
| 5,474,544 A | 12/1995 | Lynn | 604/283 |
| 5,509,433 A | 4/1996 | Paradis | 137/1 |
| 5,509,912 A | 4/1996 | Vaillancourt et al. | 604/283 |
| 5,520,665 A | 5/1996 | Fleetwood | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,540,661 A | 7/1996 | Tomisaka et al. | 604/265 |
| 5,549,566 A | 8/1996 | Elias et al. | 604/167 |
| 5,569,209 A | 10/1996 | Roitman | 604/190 |
| 5,569,235 A | 10/1996 | Ross et al. | 604/403 |
| 5,573,516 A | 11/1996 | Tyner | 604/249 |
| 5,578,059 A | 11/1996 | Patzer | 604/249 |
| 5,613,663 A | 3/1997 | Schmidt et al. | 251/149.2 |
| 5,616,129 A | 4/1997 | Mayer | 604/167 |
| 5,616,130 A | 4/1997 | Mayer | 604/167 |
| 5,620,434 A | 4/1997 | Brony | 604/406 |
| 5,674,206 A | 10/1997 | Allton et al. | 604/249 |
| 5,676,346 A | 10/1997 | Leinsing | 251/149.1 |
| 5,685,842 A | 11/1997 | Drivas | 604/49 |
| 5,685,866 A | 11/1997 | Lopez | 604/249 |
| 5,694,686 A | 12/1997 | Lopez | 29/890.126 |
| 5,695,466 A | 12/1997 | Lopez et al. | 604/93 |
| 5,699,821 A | 12/1997 | Paradis | 137/1 |
| 5,700,248 A | 12/1997 | Lopez | 604/249 |
| 5,730,418 A | 3/1998 | Feith et al. | 251/149.6 |
| 5,749,861 A | 5/1998 | Guala et al. | 604/249 |
| RE35,841 E | 7/1998 | Frank et al. | 604/256 |
| 5,788,215 A | 8/1998 | Ryan | 251/149.6 |
| 5,806,831 A | 9/1998 | Paradis | 251/149.1 |
| 5,817,069 A | 10/1998 | Arnett | 604/256 |
| 5,820,601 A | 10/1998 | Mayer | 604/167 |
| 5,921,264 A | 7/1999 | Paradis | 137/15 |
| 5,954,313 A | 9/1999 | Ryan | 251/149.1 |
| 6,029,946 A | 2/2000 | Doyle | 251/149.1 |
| 6,036,171 A | 3/2000 | Weinheimer et al. | 251/149.1 |
| 6,039,302 A | 3/2000 | Cote, Sr. et al. | 251/149.1 |
| 6,048,335 A | 4/2000 | Mayer | 604/167 |
| 6,050,978 A | 4/2000 | Orr et al. | 604/249 |
| 6,063,062 A | 5/2000 | Paradis | 604/249 |
| 6,068,011 A | 5/2000 | Paradis | 137/1 |
| 6,079,432 A | 6/2000 | Paradis | 137/1 |
| 6,089,541 A | 7/2000 | Weinheimer et al. | 251/149.6 |
| 6,152,900 A | 11/2000 | Mayer | 604/167 |
| 6,158,458 A | 12/2000 | Ryan | 137/515.5 |
| 6,189,859 B1 | 2/2001 | Rohrbough et al. | 251/149.1 |
| 6,206,860 B1 | 3/2001 | Richmond | 604/246 |
| 6,228,069 B1 | 5/2001 | Barth et al. | 604/249 |
| 6,245,048 B1 | 6/2001 | Fangrow, Jr. et al. | 604/249 |
| 6,290,206 B1 | 9/2001 | Doyle | 251/149.1 |
| 6,344,033 B1 | 2/2002 | Jepson et al. | 604/256 |
| 6,428,520 B1 | 8/2002 | Lopez et al. | 604/249 |
| 6,485,472 B1 | 11/2002 | Richmond | 604/246 |
| 6,543,745 B1 | 4/2003 | Enerson | 251/149.7 |
| 6,581,906 B2 | 6/2003 | Pott et al. | 251/149.1 |
| 6,585,229 B2 | 7/2003 | Cote, Sr. et al. | 251/149.1 |
| 6,595,964 B2 | 7/2003 | Finley et al. | 604/246 |
| 6,595,981 B2 | 7/2003 | Huet | 604/523 |
| 6,609,696 B2 | 8/2003 | Enerson | 251/86 |
| 6,626,418 B2 | 9/2003 | Kiehne | 251/149.6 |

| | | | | | |
|---|---|---|---|---|---|
| 6,669,673 B2 | 12/2003 | Lopez .................. 604/249 | 2006/0142735 A1 | 6/2006 | Whitley .................. 604/537 |
| 6,755,391 B2 | 6/2004 | Newton et al. ...... 251/149.6 | 2008/0275405 A1 | 11/2008 | Newton et al. ........ 604/256 |
| 6,869,426 B2 | 3/2005 | Ganem ................. 604/533 | | | |
| 6,883,778 B1 | 4/2005 | Newton et al. ...... 251/149.1 | FOREIGN PATENT DOCUMENTS | | |
| 6,892,998 B2 | 5/2005 | Newton ............... 251/149.1 | | | |
| 7,014,169 B2 | 3/2006 | Newton et al. ...... 251/149.6 | EP | 1243285 | 9/2002 |
| 7,037,302 B2 | 5/2006 | Vaillancourt .......... 604/533 | GB | 2079162 | 1/1982 |
| 7,100,890 B2 | 9/2006 | Cote, Sr. et al. .... 251/149.1 | WO | WO 83/02559 | 8/1983 |
| 7,396,348 B2 | 7/2008 | Newton et al. ........ 604/256 | WO | WO 93/11828 | 6/1993 |
| 2002/0024036 A1 | 2/2002 | Rohrbough et al. ... 251/149.1 | WO | WO 96/00107 | 1/1996 |
| 2003/0050610 A1 | 3/2003 | Newton et al. ........ 604/256 | WO | WO 97/39791 | 10/1997 |
| 2003/0060779 A1 | 3/2003 | Richmond ............. 604/256 | WO | WO 98/22178 | 5/1998 |
| 2003/0093061 A1 | 5/2003 | Ganem ................. 604/533 | WO | WO 98/26835 | 6/1998 |
| 2003/0098430 A1 | 5/2003 | Leinsing et al. ..... 251/149.6 | WO | WO 98/39594 | 9/1998 |
| 2003/0141477 A1 | 7/2003 | Miller ................. 251/149.1 | WO | WO 00/44433 | 8/2000 |
| 2004/0073171 A1 | 4/2004 | Rogers et al. ...... 604/164.13 | WO | WO 03/018104 A2 | 3/2003 |
| 2004/0138626 A1 | 7/2004 | Cote, Sr. et al. ....... 604/249 | WO | WO 03/018105 A1 | 3/2003 |
| 2005/0165365 A1 | 7/2005 | Newton et al. ........ 604/246 | WO | WO 2004/060466 | 7/2004 |

VALVE WITH INTERNAL LIFTER

PRIORITY

This patent application claims priority from provisional U.S. patent application No. 60/644,068, filed Jan. 14, 2005, entitled, "VALVE WITH INTERNAL LIFTER," and naming Andrew L. Cote and Brian L Newton as inventors, the disclosure of which is incorporated herein, in its entirety, by reference.

RELATED APPLICATIONS

This application is related to the following U.S. patents and U.S. patent applications, the disclosures of which are incorporated herein, in their entireties, by reference:
U.S. Pat. No. 6,039,302;
U.S. Pat. No. 6,883,778;
U.S. Pat. No. 6,755,391;
U.S. application Ser. No. 10/224,299;
U.S. Pat. No. 6,869,426;
U.S. application Ser. No. 10/687,515; and
U.S. application Ser. No. 10/700,344.

FIELD OF THE INVENTION

The invention generally relates to medical products and, more particularly, the invention relates to substantially eliminating undesired fluid drawback through a medical valve.

BACKGROUND OF THE INVENTION

In general terms, medical valving devices often act as a sealed port that may be repeatedly accessed to non-invasively inject fluid into (or withdraw fluid from) a patient's vasculature. Consequently, a medical valve acting as a fluid port permits the patient's vasculature to be freely accessed without requiring such patient's skin be repeatedly pierced by a needle.

More specifically, after it is inserted into a medical valve, a syringe may freely inject or withdraw fluid from the patient. Problems arise, however, when the syringe is withdrawn from the valve. Specifically, a back pressure (i.e., a proximally directed pressure) produced by the withdrawing syringe undesirably can draw blood proximally into the valve or a catheter connected to the valve. In addition to coagulating and impeding the mechanical operation of the valve, blood in the valve also compromises the sterility of the valve and/or catheter.

SUMMARY OF THE INVENTION

In accordance with one aspect of the invention, a medical valve having a closed mode and an open mode includes a housing having a proximal end, a distal end, and an interior. The valve also has a valve mechanism within the interior. In illustrative embodiments, the valve mechanism has a gland member and a lifter member. The lifter member moves the gland member toward the proximal end of the housing as the valve transitions from the closed mode to the open mode.

BRIEF DESCRIPTION OF THE DRAWINGS

The foregoing and advantages of the invention will be appreciated more fully from the following further description thereof with reference to the accompanying drawings wherein.

DESCRIPTION OF ILLUSTRATIVE EMBODIMENTS

In illustrative embodiments of the invention, a valve produces a positive, distally directed pressure (i.e., toward its outlet) when a nozzle or syringe is withdrawn. Such pressure should prevent non-negligible amounts of fluid from being drawn into the valve at such time. To these ends, the valve has an interior fluid chamber/flow channel sized and configured 1) to expand its volume as the valve transitions toward the open mode, and 2) to reduce its volume as the valve transitions toward the closed mode. Details of this and related embodiments also are discussed below.

Figure 1:
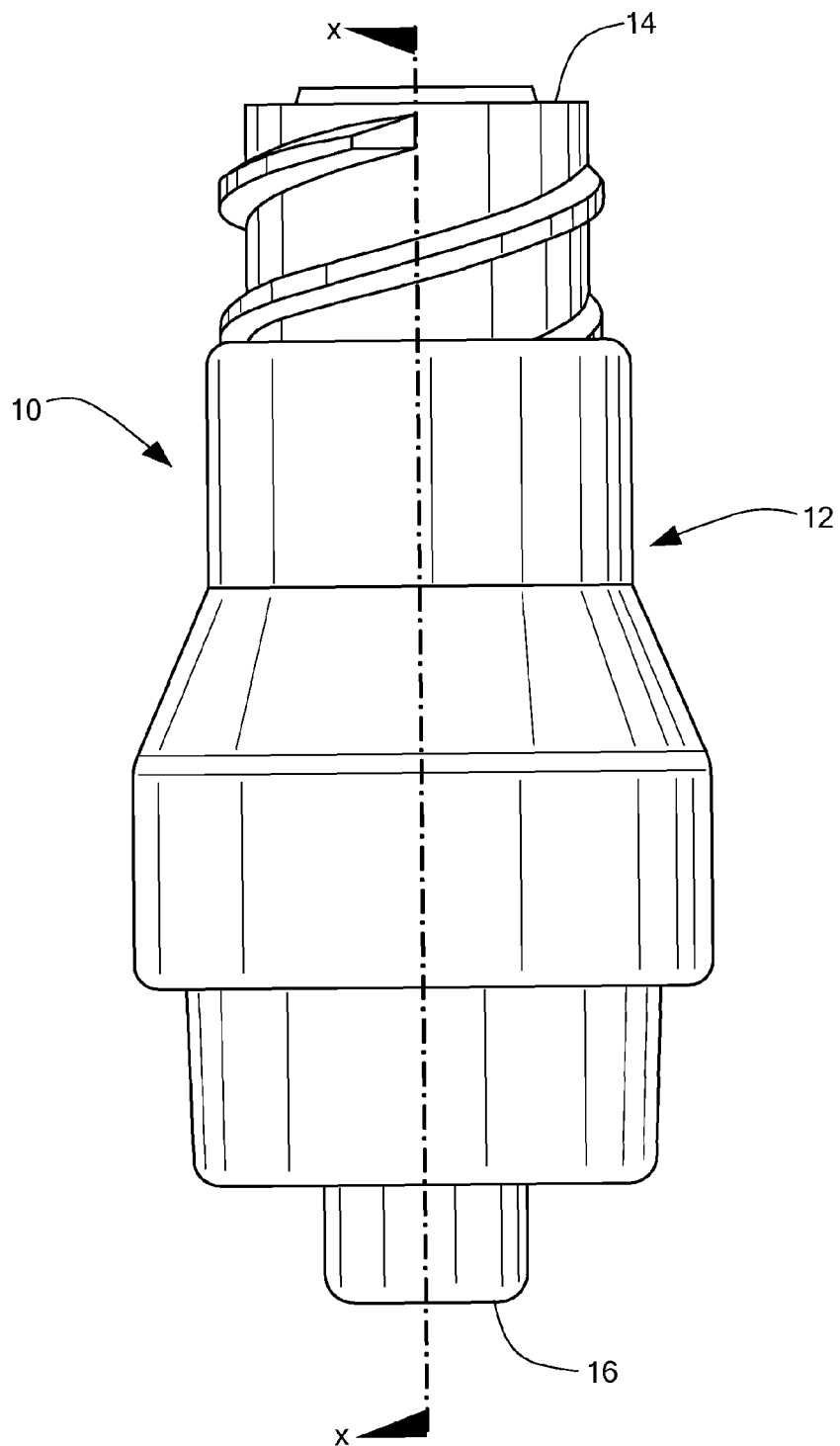
FIG. 1 schematically shows an isometric view of a medical valve that may be configured in accordance with illustrative embodiments of the invention.

FIG. 1 schematically shows a medical valve 10 that is configured to reduce fluid drawback (a.k.a. "back-flow," noted above) when a syringe or other type of nozzle is withdrawn from it. The valve 10 has a valve body/housing 12 with proximal and distal ports 14 and 16 (also respectively referred to herein as "inlet 14" and "outlet 16"). The valve body has an internal chamber 18 containing a valve element (shown in FIGS. 2A, 2B, 2C, 2D, 3A, 3B, 3C, and 3D) that controls fluid flow through the valve 10. The fluid preferably is in liquid form, such as saline or a liquid medication, to pass through a centrally formed fluid channel that extends between the inlet 14 and the outlet 16. Although much of the discussion herein refers to the proximal port 14 as a fluid inlet, and the distal port 16 as a fluid outlet, the proximal and distal ports 14 and 16 also may be respectively used as outlet and inlet ports.

Figure 2A:
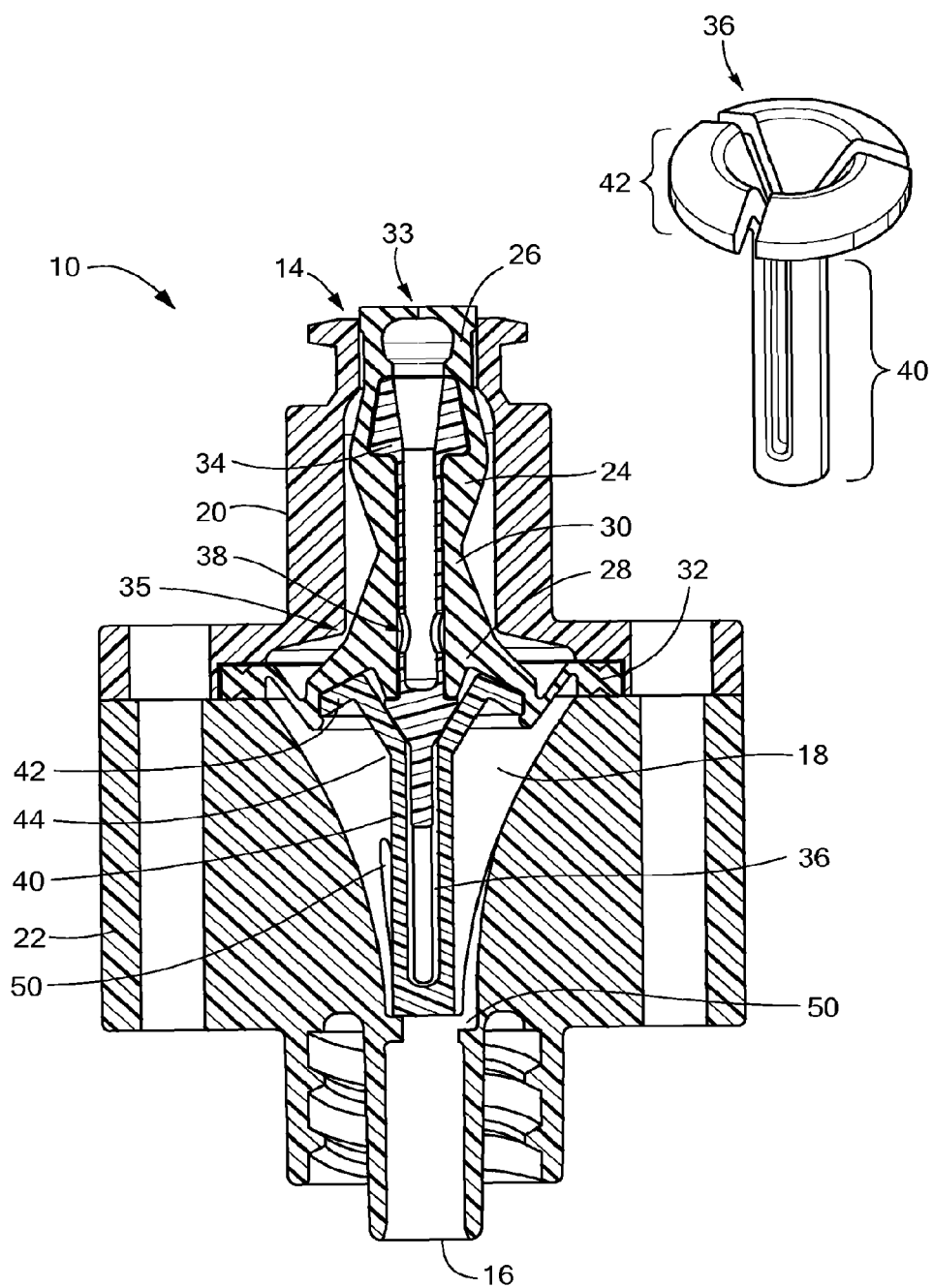
FIG. 2A schematically shows a cross-sectional view of the medical valve of FIG. 1 in accordance with a first embodiment of the invention.
Figure 3A:
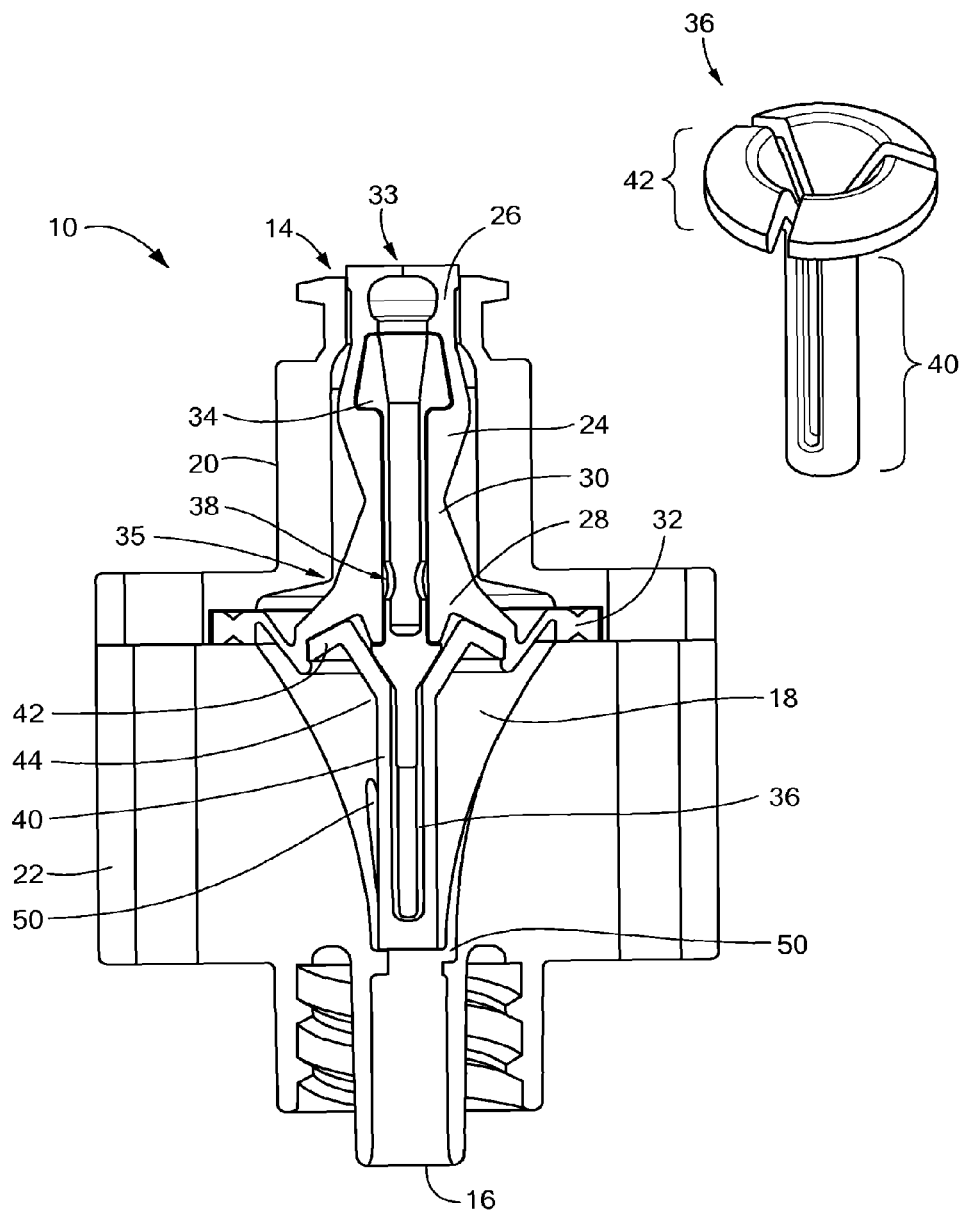
FIG. 3A schematically shows a wireframe in view of the embodiment shown in FIG. 2A.

FIGS. 2A and 3A schematically shows cross-sectional views of the valve 10 of FIG. 1 in accordance with a first embodiment of the invention. The housing 12 includes inlet and outlet housing portions 20 and 22, which illustratively are formed from a hard plastic material that are snap-fit together. For example, the housing portions 20 and 22 may be configured to snap fit together in accordance with the teachings of co-pending, commonly owned U.S. patent application Ser. No. 10/265,292, filed Oct. 4, 2002, the disclosure of which is incorporated herein, in its entirety, by reference. It should be noted that although some embodiments are discussed as being snap-fit components, various embodiments of the invention may be coupled by either snap-fit or other means, such as by ultrasonic welding. Accordingly, such embodiments are not intended to be limited to snap-fit components.

When coupled, the housing portions 20 and 22 form the internal chamber 18, which is shaped to comply with the operation of its internal valve element (discussed below). The proximal port 14, which is part of this chamber 18, illustratively is contoured to accept various types of nozzles, such as those complying with ANSI/ISO standards (e.g., luers complying with ANSI and/or ISO standards).

The valve element has a stretchable, resilient, and compressible member (referred to in various embodiments herein as "gland 24") secured between the inlet housing 20 and outlet housing 22. In illustrative embodiments, the gland 24 is formed from an elastomeric material, such as silicone or rubber. Other materials having similar properties may be used, however, so long as they can perform the functions discussed herein.

The gland 24 has several cooperating sections for controlling fluid flow through the valve 10 while substantially eliminating fluid drawback. Namely, the gland 24 has a proximal section 26 near its proximal end, a distal section 28 near its distal end, and a central section 30 between the proximal and distal sections 26 and 28. The three sections 26, 28, and 30 together form a portion of a contiguous fluid flow path that extends the length of the valve 10. In addition, the gland 24 also has an attachment section 32 for securing the gland 24 within the valve 10 and maintaining fluid flow in the flow channel. In illustrative embodiments, the proximal section 26 of the gland 24 has a slit 33 for providing a low pressure seal.

The valve element also includes a rigid and longitudinally movable cannula 34 secured within the gland 24, and a lifter 36 for urging the gland 24 proximally as the valve 10 transitions from a closed mode to an open mode.

In illustrative embodiments, the cannula 34 is a hollow needle that, together with the gland 24, form a part of the internal flow channel within the valve 10. The cannula 34 is open at its proximal end, closed at its distal end, and has holes 38 in its side just proximal to its distal end. The cannula 34 also has a protruding distal end that facilitates assembly. As shown in the Figures, when in the closed position, the holes 38 are occluded by the gland 24. An annular corner 35 of the interior chamber 18 aids in the sealing the holes 38. In addition, the slit 33 also is normally closed when the valve 10 is in the closed mode.

FIG. 2A also shows an isometric view of the lifter 36. The lifter 36 has a main body 40 supported by the base of the interior chamber 18, and a top portion 42 abutting the bottom of the gland 24. The main body 40 illustratively forms a plurality of living hinges 44 that flex as the valve 10 transitions between opened and closed modes. The lifter 36 illustratively is formed from a flexible, hard plastic.

Figure 3B:
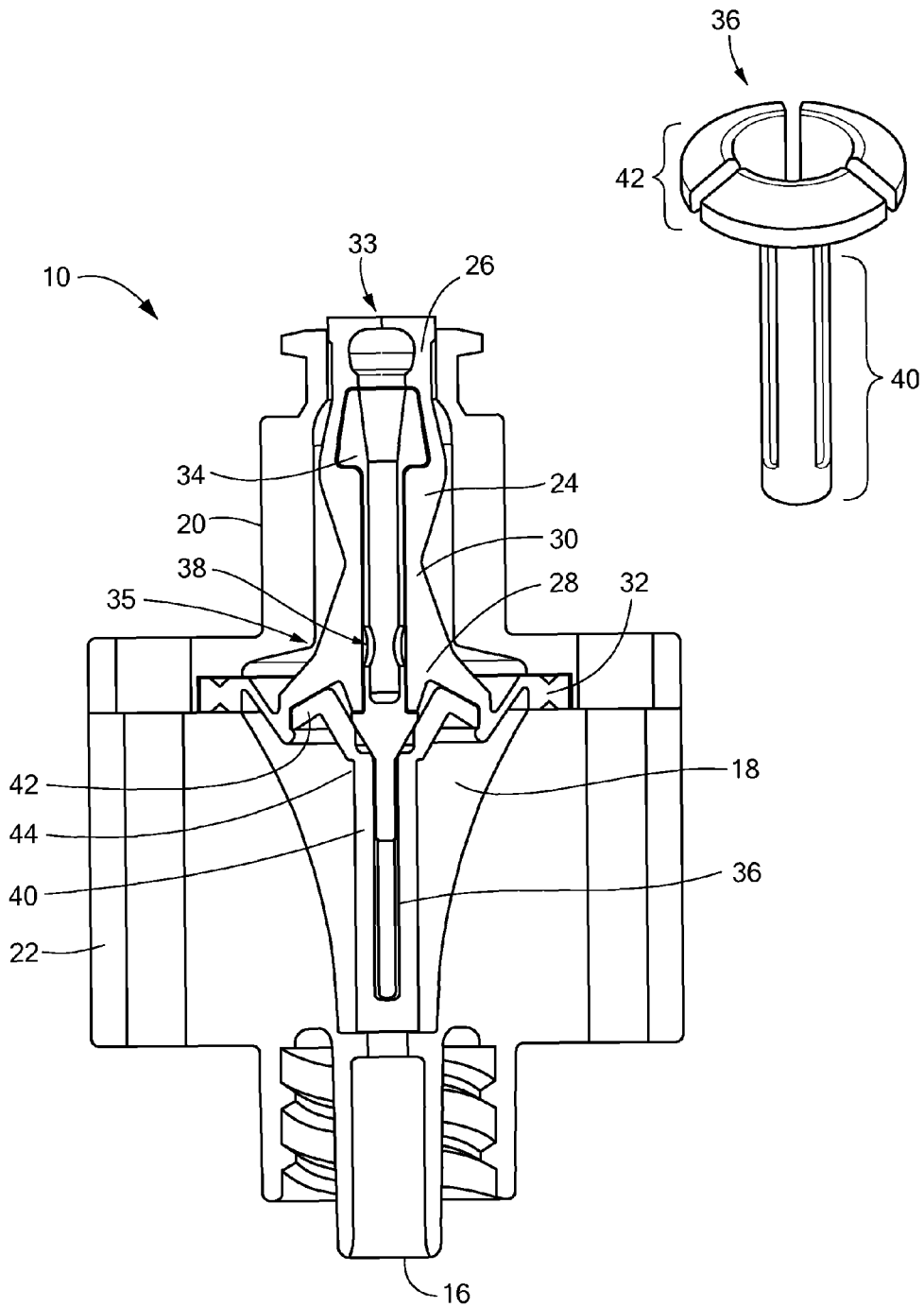
FIG. 3B schematically shows a wireframe in view of the embodiment shown in FIG. 2B.
Figure 3C:
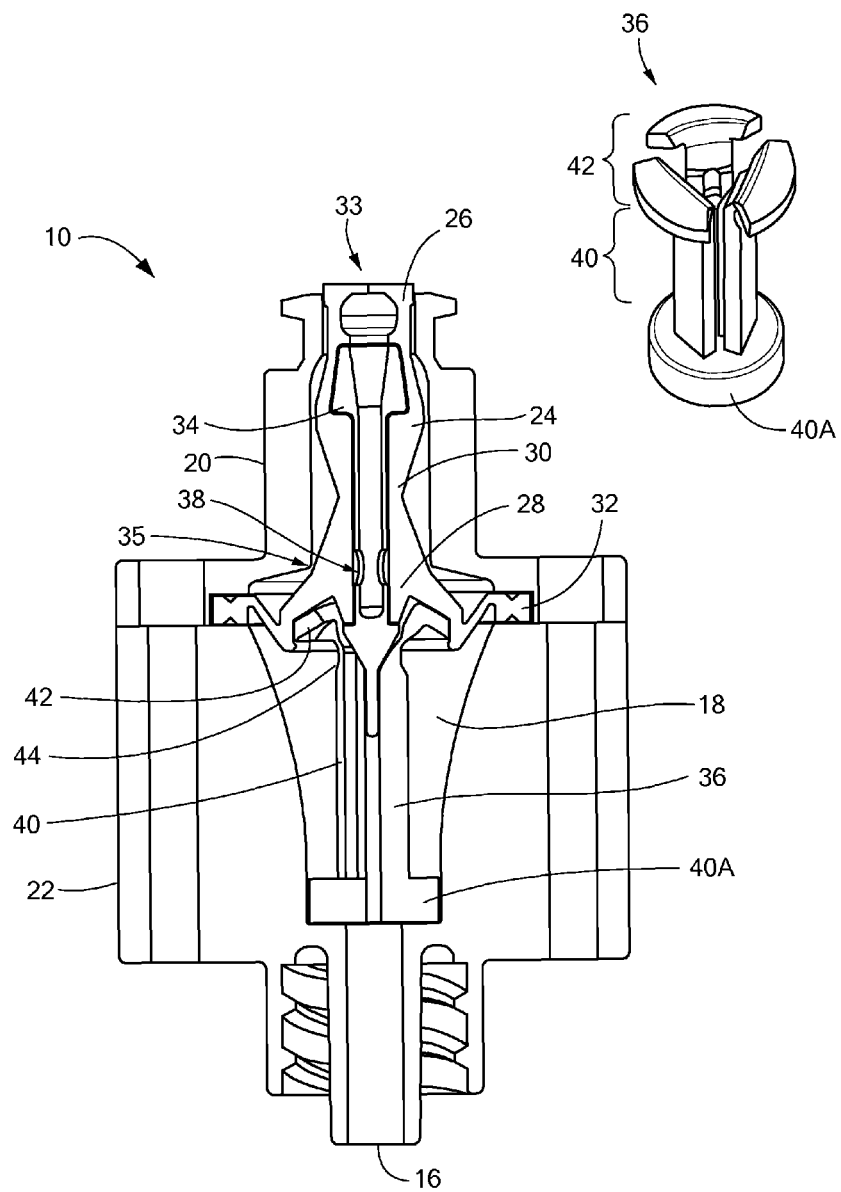
FIG. 3C schematically shows a wireframe in view of the embodiment shown in FIG. 2C.

When the valve 10 is in the fully closed position, the proximal section 26 of the gland 24 is flush with, or extends slightly above, the exterior inlet face of the housing 12 (see, for example, FIGS. 3A and 3B). The proximal section 26 and the exterior inlet face thus present a swabbable surface. In other words, the proximal section 26 and the exterior inlet face may be easily wiped clean by any conventional means, such as with an alcohol swab. As mentioned in the above noted incorporated patent, valves having swabbable surfaces are known in the art as "swabbable valves." In other embodiments, however, the valve 10 is not a swabbable valve.

Insertion of a nozzle (e.g., a luer 52) into the proximal port 14 forces the gland 24 to move (radially and longitudinally, as discussed below) to an open position. When in that position, a flow channel from the proximal port to the distal port 16 is considered to be formed as follows:

First through the proximal port 14 and the slit 33 in the proximal section 26,
Then through the interior of the gland 24 to the open end of the cannula 34,
Through the cannula channel to the cannula holes 38, into internal chamber 18 and through chamber channel 50,
Through a distal hole in the housing 12 to an outlet channel terminating at the distal port 16.

To open this fluid channel, the proximal section 26 of the gland 24 collapses onto the top surface of the cannula 34 to open the slit 33. The cannula 34 also begins traversing distally, thus prying the main body 40 of the lifter 36 radially outwardly. Consequently, the main body 40 of the lifter 36 flexes about the three living hinges 44. This causes the top portion 42 of the lifter 36 to move proximally. Due to their spatial relationship, this lifter movement thus urges the bottom portion of the gland 24 proximally. Accordingly, the overall fluid volume within the flow channel increases.

Removal of the nozzle has a corresponding effect of decreasing the overall flow channel volume. Specifically, as the valve element returns toward the closed position, the gland 24 returns to its relaxed state, which reduces overall internal chamber 18 of volume. As noted above, this volume change should produce a positively directed pressure toward the distal port 16. Such positive pressure consequently should substantially eliminate fluid drawback into the valve 10 or its attached catheter.

It should be noted, however, that the actual volume of the flow channel is anticipated to vary as the valve element moves proximally. In fact, during the return cycle, there could be times when fluid is drawn toward or back into the valve 10 and/or catheter. In illustrative embodiments, however, the overall volume change has a net effect of producing a net positive pressure through the outlet 16, thus substantially eliminating fluid drawback.

Figure 2B:
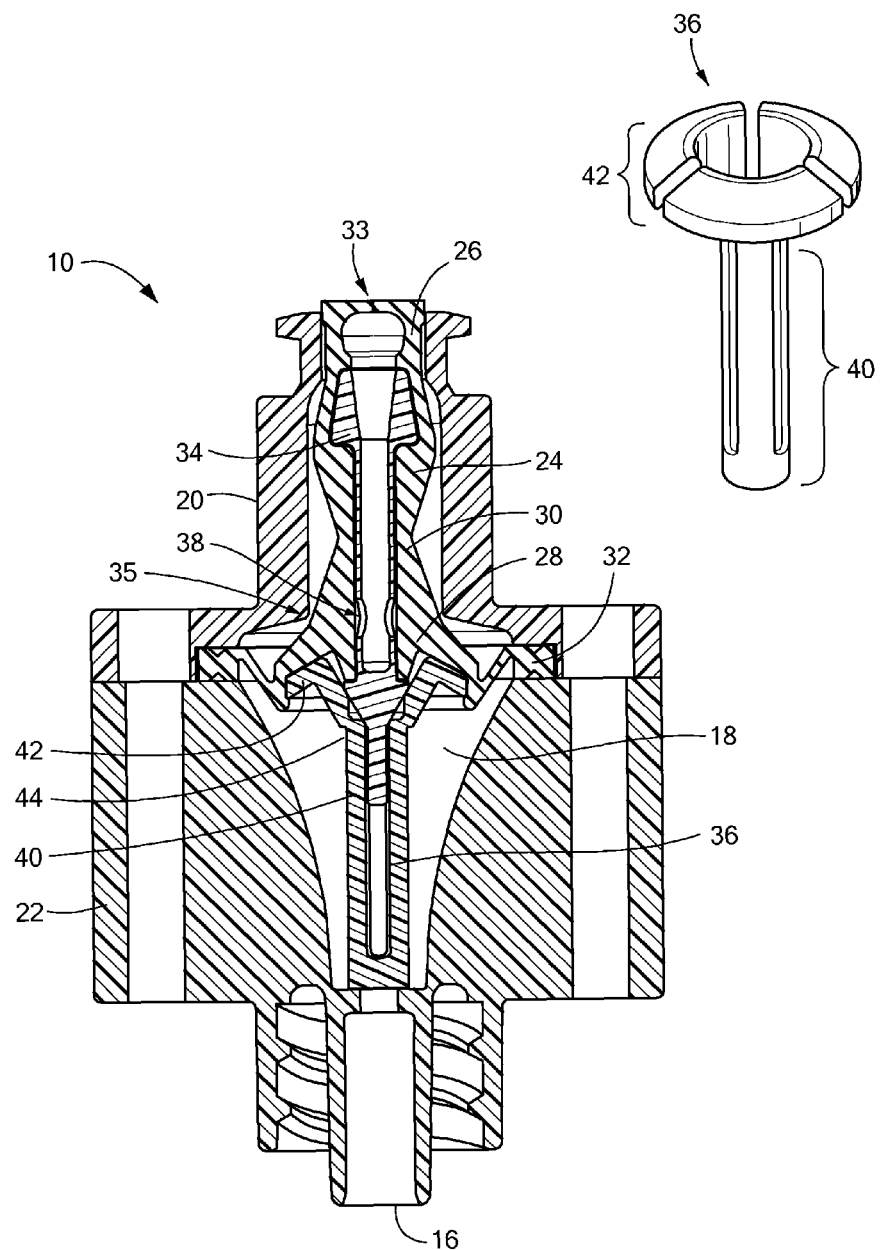
FIG. 2B schematically shows a cross-sectional view of the medical valve of FIG. 1 in accordance with a second embodiment of the invention.
Figure 2C:
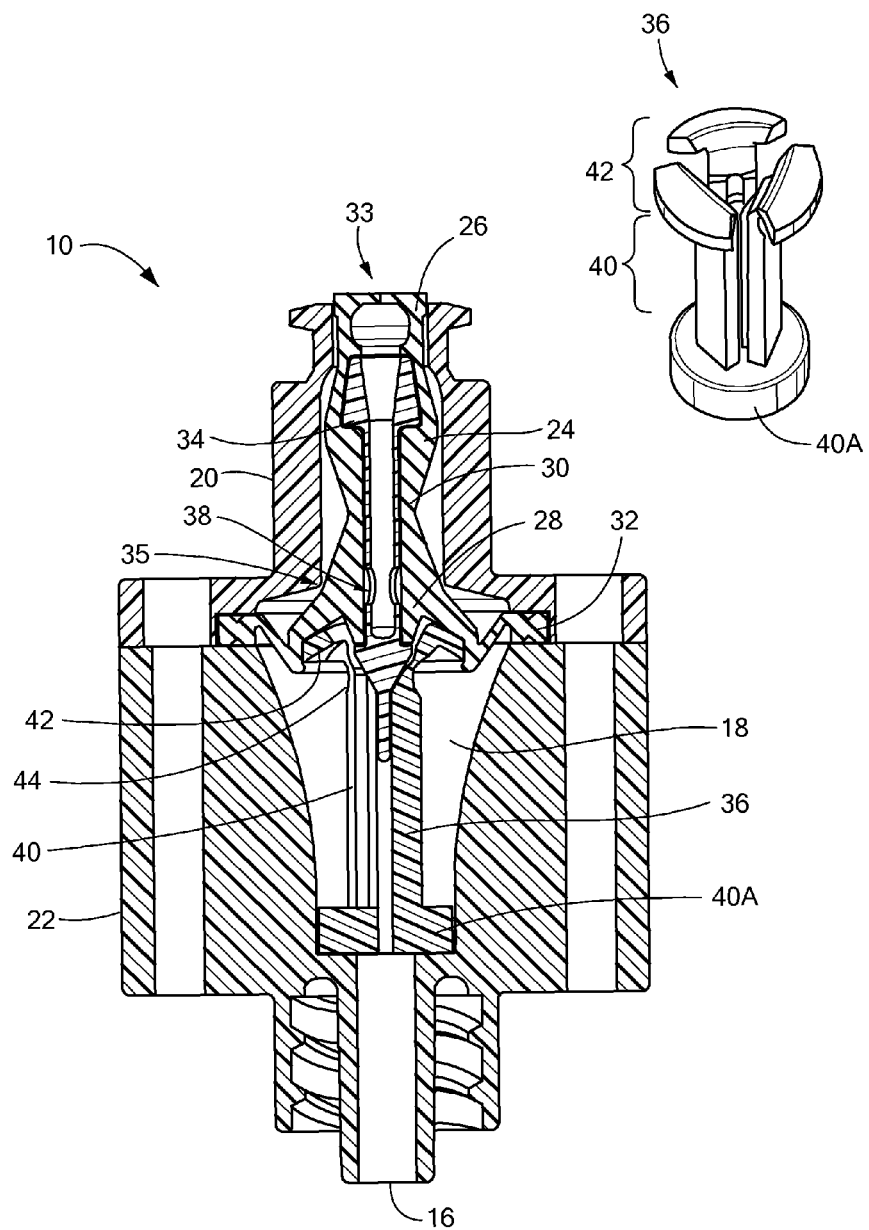
FIG. 2C schematically shows a cross-sectional view of the medical valve of FIG. 1 in accordance with a third embodiment of the invention.
Figure 2D:
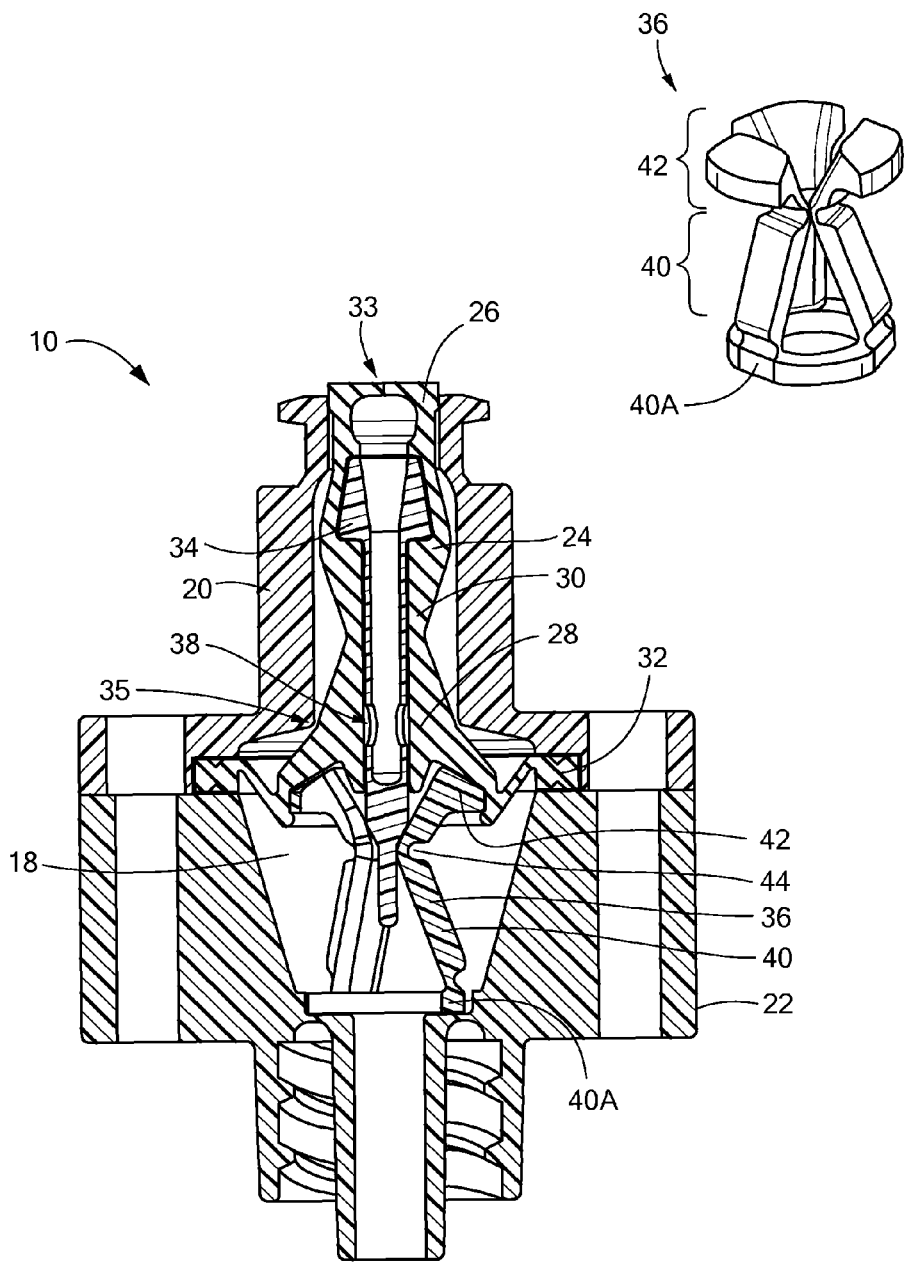
FIG. 2D schematically shows a cross-sectional view of the medical valve of FIG. 1 in accordance with a fourth embodiment of the invention.
Figure 2E:
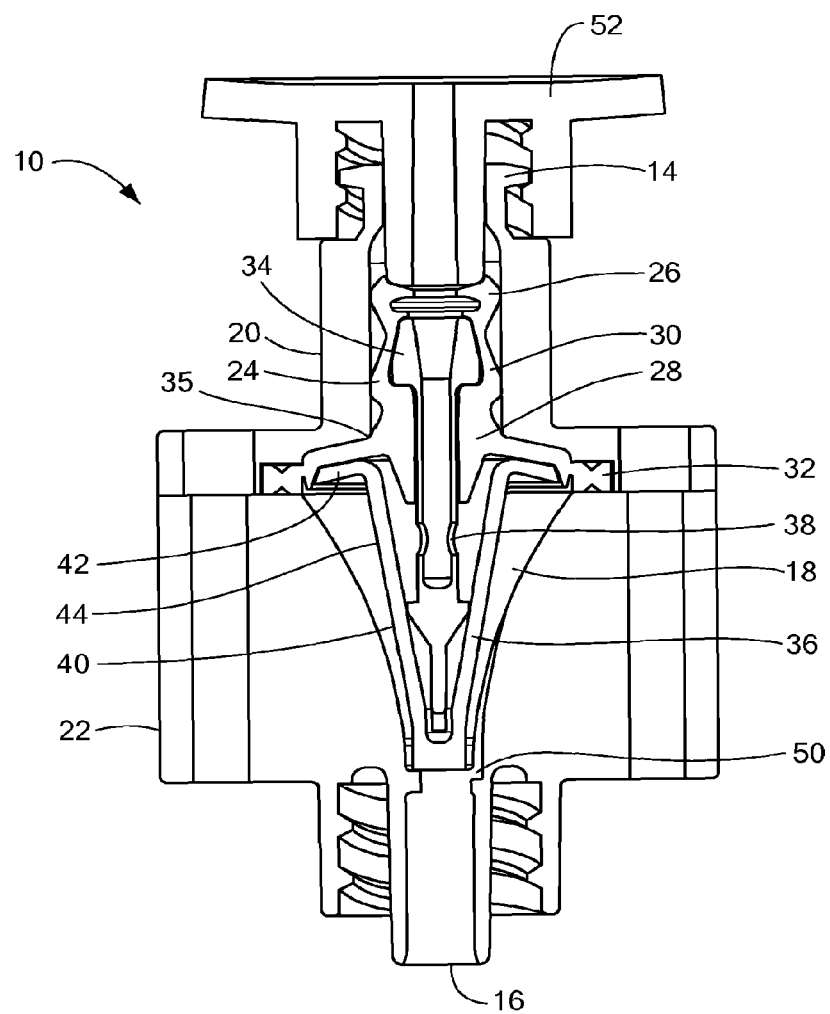
FIG. 2E schematically shows a cross-sectional view of the medical valve of FIG. 1 in the open mode in accordance with embodiments of the invention.

FIGS. 2B, 2C, 2D and their corresponding wireframe representations show alternate embodiments of the invention. For example, FIGS. 2B and 3B have a different hinge structure than that shown in FIGS. 2A and 3A. Specifically, unlike the hinges 44 shown in FIG. 2A, each of the hinges 44 shown in FIG. 2B has a specialized contour and varying thickness.

In a manner similar to in FIG. 2B, the hinges 44 in FIG. 2C also are specially contoured. In addition, the lifter 36 also has a radial base 40A to provide better support within the interior chamber 18.

Figure 3D:
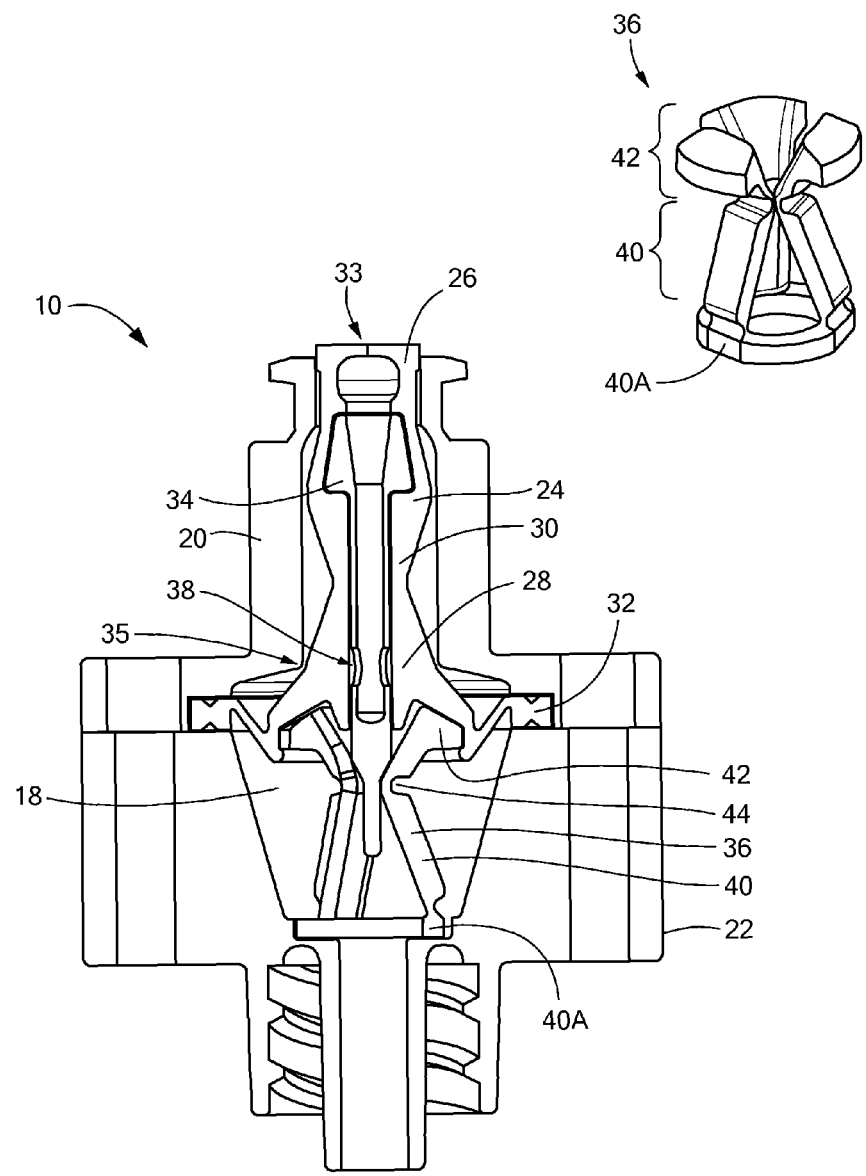
FIG. 3D schematically shows a wireframe in view of the embodiment shown in FIG. 2D.

FIGS. 2D and 3D schematically show yet another embodiment of the lifter 36. In a manner similar to other embodiments, this embodiment also has specially contoured hinges 44. Unlike other embodiments, however, both the main body 40 and the top portion 42 taper radially inwardly as they approach the hinges 44. It is anticipated that this tapered design will proximally displace the gland 24 in a more efficient and controllable manner.

Although the above discussion discloses various exemplary embodiments of the invention, it should be apparent that those skilled in the art can make various modifications that will achieve some of the advantages of the invention without departing from the true scope of the invention.

What is claimed is:

1. A medical valve having a closed mode and an open mode, the valve comprising:
a housing having a proximal end, a distal end, and an interior;
a valve mechanism within the interior, the valve mechanism including a gland member and a movable lifter member, the lifter member moving at least a portion of the gland member toward the proximal end of the housing as the valve transitions from the closed mode toward the open mode, the closed mode preventing fluid flow through the valve, the open mode permitting fluid flow through the valve.

2. The medical valve as defined by claim 1 wherein the housing forms a fluid channel having an internal chamber, the internal chamber being at least a portion of the fluid channel, proximal movement of the gland member by the lifter member causing the internal chamber to have an increasing volume.

3. The medical valve as defined by claim 1 wherein the housing forms a fluid channel within the interior, the fluid channel having an internal chamber having a decreasing size as the valve transitions from the open mode toward the closed mode.

4. The medical valve as defined by claim 3 wherein the housing has an outlet port, the decreasing size of the internal chamber producing a distally directed pressure through the outlet port.

5. The medical valve as defined by claim 4 wherein the volume of the fluid channel decreases as the internal chamber size decreases, the decreasing fluid channel volume and decreasing internal chamber volume producing the distally directed pressure through the outlet port.

6. The medical valve as defined by claim 1 wherein the lifter member has an arm with a living hinge, the arm being in contact with the gland member.

7. The medical valve as defined by claim 1 wherein the valve mechanism includes a cannula coupled to the gland member, the cannula and gland member forming two spaced apart seals.

8. The medical valve as defined by claim 1 wherein the gland member forms a swabbable surface with the housing.

9. The medical valve as defined by claim 1 wherein the housing forms a fluid channel within the interior, the fluid channel having an internal chamber having a decreasing size as the valve transitions from the open mode toward the closed mode.

10. The medical valve as defined by claim 9 wherein the housing has an outlet port, the decreasing size of the internal chamber producing a positive pressure through the outlet port.

11. The medical valve as defined by claim 10 wherein the volume of the fluid channel decreases as the internal chamber volume decreases, the decreasing fluid channel volume and decreasing internal chamber volume producing the positive pressure through the outlet port.

12. The medical valve as defined by claim 10 wherein the gland and lifting means includes means for producing a distally directed pressure through the distal end as the valve moves from the open mode toward the closed mode.

13. The medical valve as defined by claim 1 wherein the valve prevents fluid flow through the valve when in the closed mode.

14. The medical valve as defined by claim 1 wherein the valve transitions from the closed mode to the open mode after insertion of a medical implement into an inlet of the medical valve.

15. A medical valve having a closed mode and an open mode, the valve comprising:
   a housing having a proximal end, a distal end, and an interior;
   means for valving fluid through the interior,
   the valving means including a gland member and lifting means, the lifting means moving at least a portion of the gland member toward the proximal end of the housing as the valve transitions from the closed mode to the open mode, the closed mode preventing fluid flow through the valve, the open mode permitting fluid flow through the valve.

* * * * *